(12) United States Patent
Gerosolimo et al.

(10) Patent No.: US 10,531,879 B2
(45) Date of Patent: Jan. 14, 2020

(54) SURGICAL CLAMPING DEVICES

(71) Applicant: VASCULAR DEVICES PTY. LTD., Balwyn East, Victoria (AU)

(72) Inventors: Albert Gerosolimo, Bulleen (AU); Ian Reilly, Mount Waverley (AU); Geoffrey Paul Whelan, Surrey Hills (AU)

(73) Assignee: VASCULAR DEVICES PTY. LTD., Victoria (AU)

( * ) Notice: Subject to any disclaimer, the term of this patent is extended or adjusted under 35 U.S.C. 154(b) by 237 days.

(21) Appl. No.: 15/554,798

(22) PCT Filed: Mar. 3, 2016

(86) PCT No.: PCT/AU2016/050139
§ 371 (c)(1),
(2) Date: Aug. 31, 2017

(87) PCT Pub. No.: WO2016/138562
PCT Pub. Date: Sep. 9, 2016

(65) Prior Publication Data
US 2018/0042613 A1 Feb. 15, 2018

(30) Foreign Application Priority Data
Mar. 3, 2015 (AU) .................. 2015900733

(51) Int. Cl.
*A61B 17/122* (2006.01)
*A61B 17/128* (2006.01)
(Continued)

(52) U.S. Cl.
CPC .......... *A61B 17/122* (2013.01); *A61B 17/128* (2013.01); *A61B 17/1285* (2013.01);
(Continued)

(58) Field of Classification Search
CPC . A61B 17/122; A61B 17/1285; A61B 17/135; A61B 17/1322
See application file for complete search history.

(56) References Cited

U.S. PATENT DOCUMENTS

| | | |
|---|---|---|
| 3,538,917 A | 11/1970 | Selker |
| 4,120,302 A | 10/1978 | Ziegler |

(Continued)

FOREIGN PATENT DOCUMENTS

| | | |
|---|---|---|
| EP | 1562492 | 1/2007 |
| EP | 1878390 | 4/2009 |
| WO | 2009/048367 | 4/2009 |

OTHER PUBLICATIONS

International Search Report and Written Opinion from PCT/AU16/50139 dated May 5, 2016.

*Primary Examiner* — Tuan V Nguyen
(74) *Attorney, Agent, or Firm* — Calfee, Halter & Griswold LLP

(57) ABSTRACT

Clamping devices for occluding a blood vessel comprise a pair of jaws for receiving the blood vessel therebetween, one or more inflatable membranes within the jaws and at least one handle coupled to the pair of jaws via a hollow arm. The at least one handle comprises an actuator coupled to the one or more inflatable membranes via the hollow arm for inflating the one or more inflatable membranes to occlude the blood vessel.

16 Claims, 8 Drawing Sheets

(51) Int. Cl.
     *A61B 17/00*     (2006.01)
     *A61B 90/00*     (2016.01)
     *A61B 17/12*     (2006.01)

(52) U.S. Cl.
     CPC .......... *A61B 2017/0023* (2013.01); *A61B 2017/0046* (2013.01); *A61B 2017/00367* (2013.01); *A61B 2017/00477* (2013.01); *A61B 2017/00557* (2013.01); *A61B 2017/00862* (2013.01); *A61B 2017/00991* (2013.01); *A61B 2017/12004* (2013.01); *A61B 2090/0813* (2016.02)

(56) References Cited

U.S. PATENT DOCUMENTS

| | | | | |
|---|---|---|---|---|
| 4,708,140 | A | * | 11/1987 | Baron .................. A61B 17/12 606/158 |
| 4,800,879 | A | | 1/1989 | Goiyakhovsky et al. |
| 5,074,869 | A | * | 12/1991 | Daicoff ................ A61B 17/12 606/158 |
| 5,236,437 | A | | 8/1993 | Wilk et al. |
| 5,250,074 | A | * | 10/1993 | Wilk .................... A61B 17/12 606/158 |
| 5,624,454 | A | | 4/1997 | Palti et al. |
| 5,697,942 | A | | 12/1997 | Palti et al. |
| 5,921,996 | A | | 7/1999 | Sherman |
| 5,984,934 | A | * | 11/1999 | Ashby ................ A61B 17/1227 606/151 |
| 6,036,706 | A | | 3/2000 | Morejohn et al. |
| 6,582,451 | B1 | | 6/2003 | Marucci et al. |
| 6,656,205 | B1 | | 12/2003 | Manhes |
| 2005/0113634 | A1 | | 5/2005 | Burbank et al. |
| 2005/0113852 | A1 | | 5/2005 | Burbank et al. |

\* cited by examiner

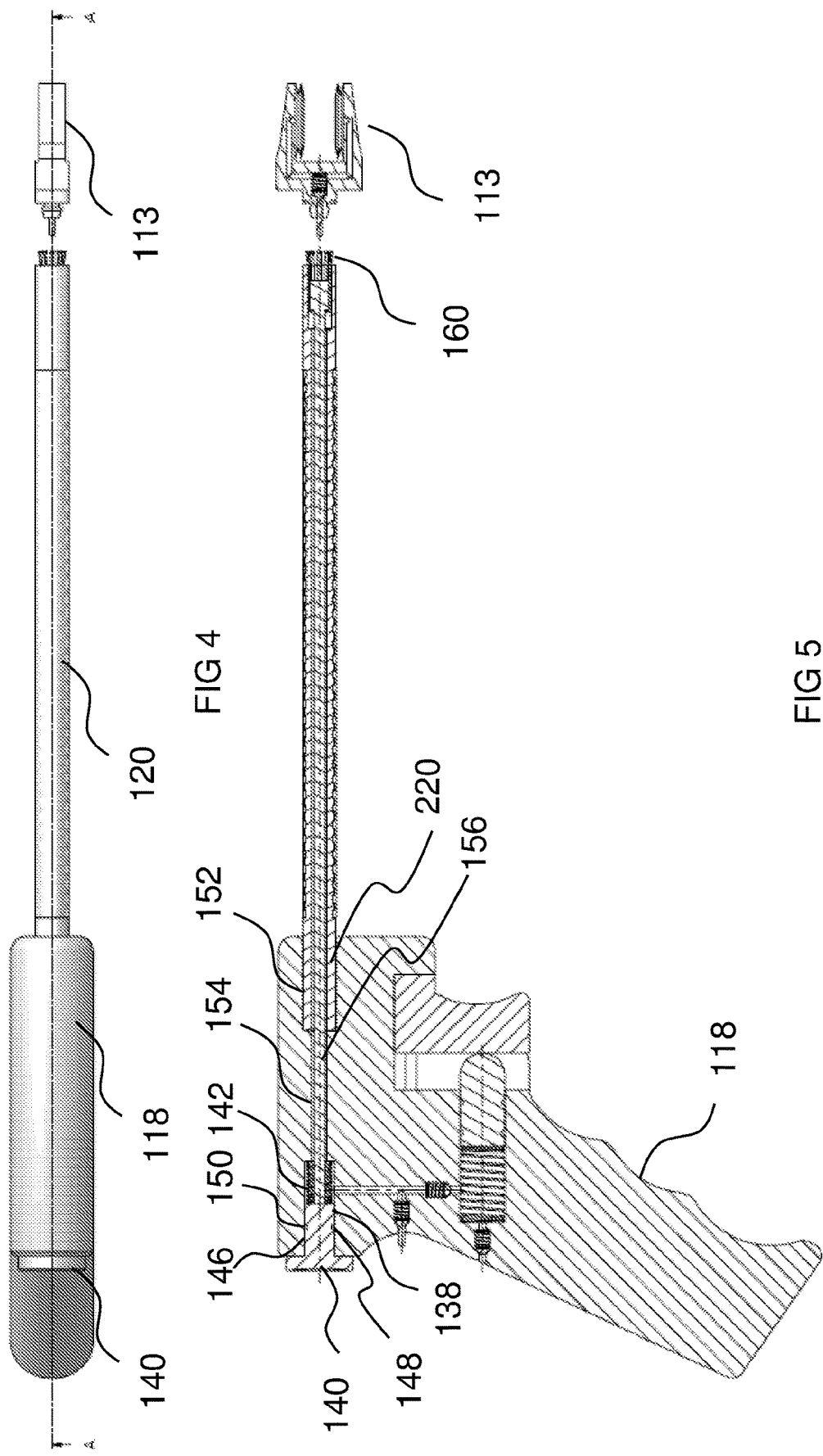

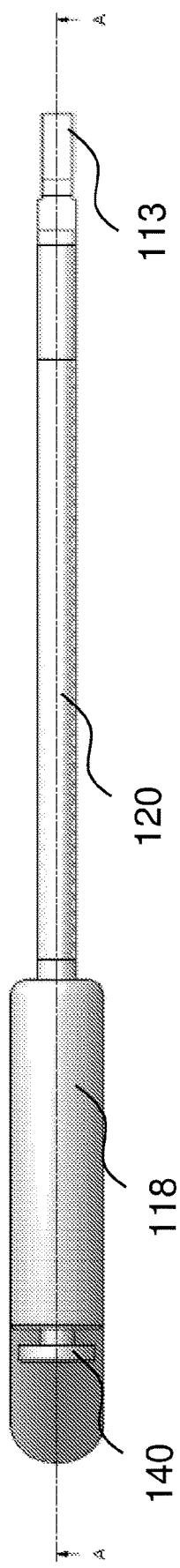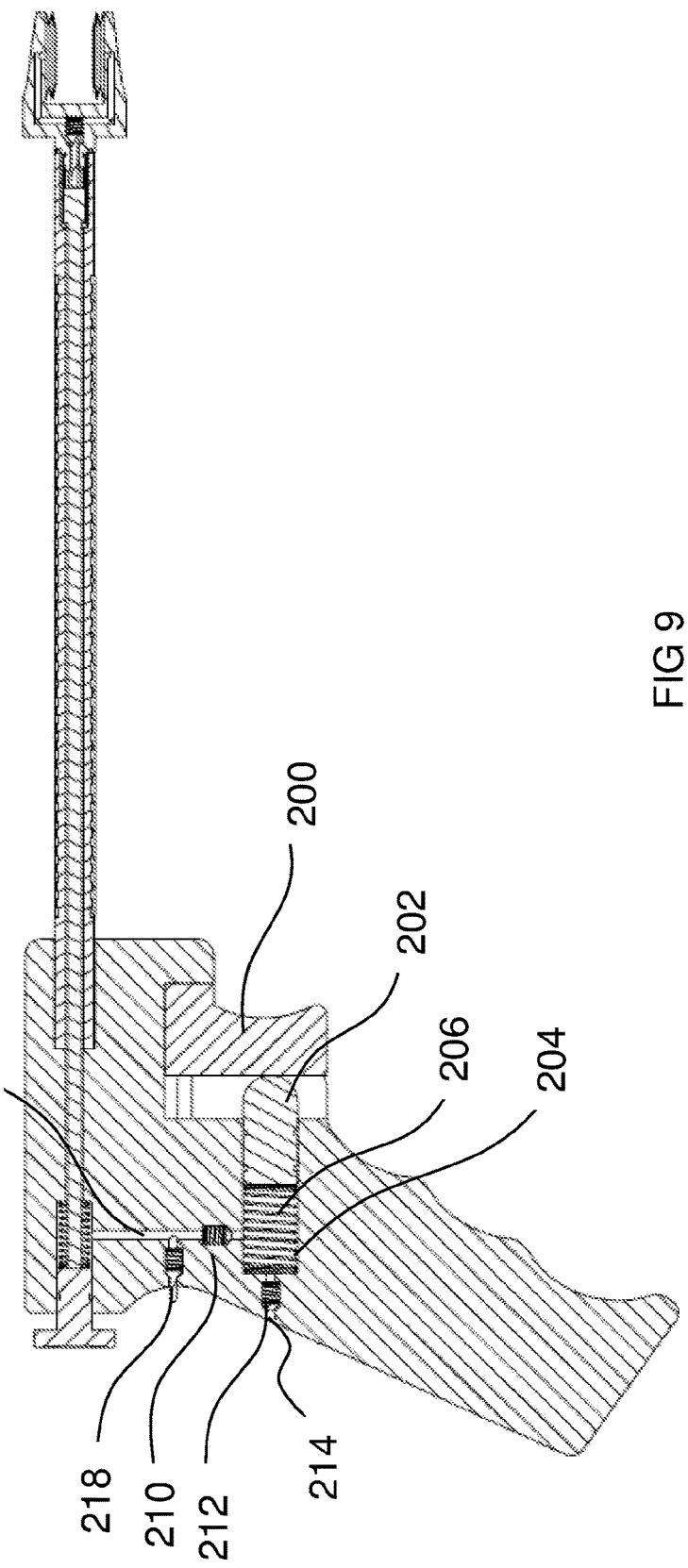
FIG 8
FIG 9

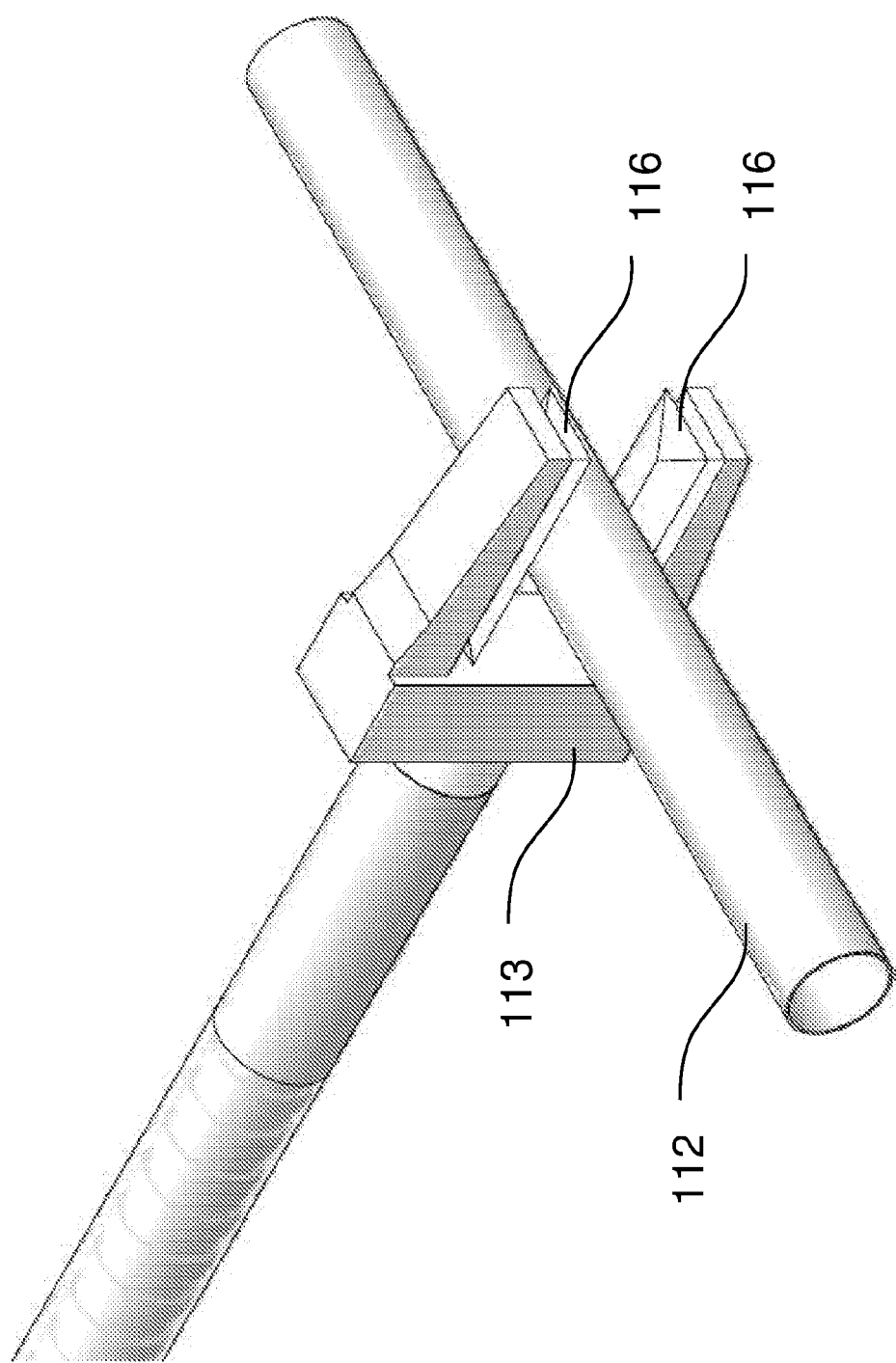

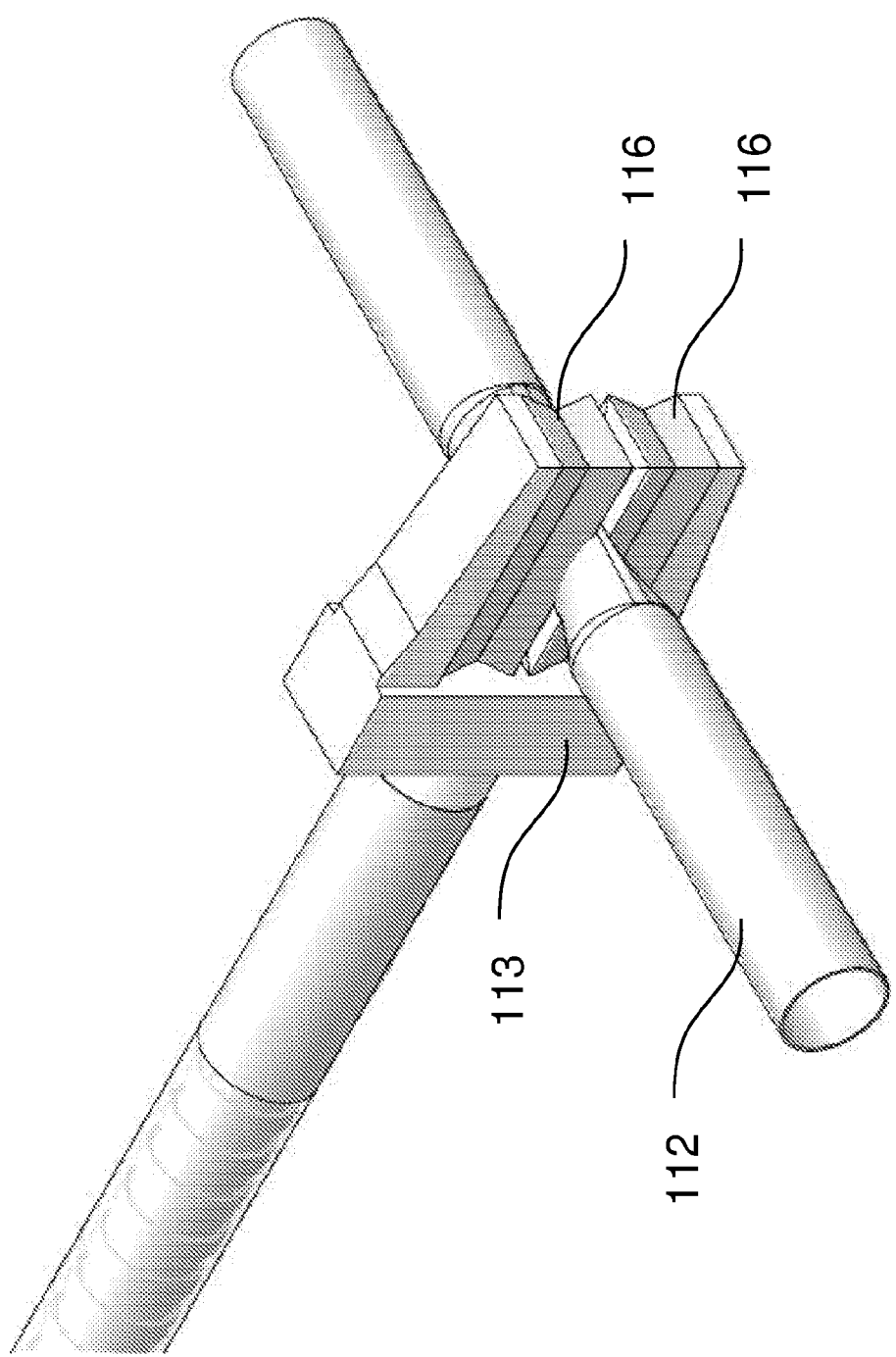

SURGICAL CLAMPING DEVICES

RELATED APPLICATIONS

The present application is the U.S. national phase entry of PCT/AU2016/050139, with an international filing date of Mar. 3, 2016, which claims the benefit of Australian Patent Application No. 2015900733, filed on Mar. 3, 2015, the entire disclosures of which are incorporated herein by reference.

FIELD OF THE INVENTION

The present invention relates to surgical clamping devices. In particular, but not exclusively, the present invention relates to devices for temporarily constricting blood vessels and/or occluding blood flow in blood vessels, such as veins, arteries and capillaries in humans and animals.

BACKGROUND OF THE INVENTION

During many surgical procedures it is necessary to temporarily constrict or occlude the blood flow in blood vessels, such as veins and arteries. This is typically achieved with a surgical clamp comprising a pair of elongate clamping members. A clamping member is positioned either side of the vein or artery, or either side of body tissue comprising the vein or artery, and the clamping members are biased towards each other to hold the vein, artery or body tissue therebetween. Biasing is typically achieved via a spring, a ratcheting mechanism or by hand depending on the type of clamping device and the location of the vein, artery or body tissue being clamped.

Blood vessel clamps, for example, are available from manufacturers in a range of sizes suited to clamping blood vessels ranging from about 0.02 mm to about 2 cm. Some clamps have a pre-set clamping tension for each respective clamp size, while other larger clamps are manually operated using a ratcheting closure system requiring the operator to estimate the appropriate level of force required to occlude blood flow in the blood vessel. Smaller clamps comprise shorter clamping members and smaller springs, which exert a lower clamping force in an effort to avoid damage to the respective blood vessels. Conversely, larger clamps comprise longer clamping members and stronger springs, which exert a higher clamping force to constrict or occlude blood flow in larger blood vessels. Such clamps can be single clamps or a pair of clamps mounted to a rod or pin and spaced apart for clamping two different locations of a single artery.

For some types of surgery, the pair of elongate clamping members is provided at the end of a pair of elongate handles, such as with forceps, such that clamping within a body cavity can be achieved more easily. In this example, the clamping members are typically retained in one of a plurality of predetermined separation positions via a releasable ratchet mechanism.

One disadvantage with the aforementioned prior art clamping devices is that the force exerted on the vein, artery or tissue by the clamping members can vary quite significantly. The ratchet or scissor-type clamps can exert a very high force because of the mechanical advantage the user has when operating them. This will depend on the size and type of clamp used, the size and type of spring or other biasing means employed, the type of vein or artery being clamped and the amount and type of tissue surrounding the vein or artery. For example, muscle has a high tensile strength whereas fat has a low tensile strength. If the force is too low, the desired level of blood flow constriction or occluded blood flow will not be achieved and if the force is too high, the vein or artery could be damaged leading to potentially life-threatening complications. Examples of such complications include thrombosis, which is caused as a result of damage to the blood vessel at the point of clamping, and heart attacks or strokes caused by dislodgement of plaque material at the clamping site.

Often the pressure exerted by the clamping members is non-uniform along their length resulting in a pressure gradient. Many clamps apply greater pressure at the approximate location of the blood vessel being clamped with less pressure being applied at the distal location of the blood vessel causing damage to the blood vessel as a result of uneven pressure being applied to the blood vessel.

Another drawback of conventional surgical clamps and in particular the manually operated clamps that are available in a range of sizes and shapes, is the cost. For example, a batch of 10 surgical clamps of a single size and shape can cost about $500. A single size of clamp may only be suitable for a specific type of surgery and such clamps are often disposable, single-use clamps. Therefore medical facilities experience significant expenditure in providing and maintaining sufficient numbers of clamps in the required range of sizes. Furthermore, a particular size of clamp may be suitable for exerting an appropriate level of force on a particular artery in one patient, but this may be excessive or insufficient for the same artery in the same procedure in a different patient, for example, due to varying levels of plaque build up between patients.

Metal surgical clamping devices can be sterilized and reused, which addresses to an extent the cost associated with replacing single use clamping devices. However, reusable metal surgical clamping devices usually have a greater initial cost. Also, at least some of the metal surgical clamping devices experience metal fatigue after repeated use, which can lead to cracks in the metal that can cause infection. Metal surgical clamps also tend to lose clamping tension due to repeated use.

Various attempts have been made to alleviate at least some of these problems. For example, EP1562492 discloses an apparatus for the detection and occlusion of blood flow comprising a pair of elongate clamping members for clamping tissue comprising an artery. The apparatus is similar to a pair of forceps and comprises a releasable ratcheting mechanism to maintain pressure between the clamping members. One of the clamping members comprises a blood flow detecting sensor to facilitate the location or monitoring of the artery to be occluded. The sensor can detect the reduction or abolition of blood flow and the releasable ratcheting mechanism can be adjusted to change the blood flow.

The apparatus of EP1562492 is particularly suited for occluding blood flow in uterine arteries. However, blood flow is still dependent on and controlled by the manual adjustment of the releasable ratcheting mechanism by the nurse or surgeon, thus still requiring the necessary skill and care in applying the correct pressure for the particular procedure, the particular region of the body and the particular patient. Furthermore, the blood flow detecting sensor is coupled to a sensor control device via a detachable cable external to the elongate arms of the device. The external cable can potentially interfere with the procedure and can present a snagging risk in relation to other apparatus or protruding elements in the operating theatre. Therefore, the external cable is considered to be undesirable. Whilst the elongate arms facilitate access to body cavities, the elongate arms render the clamping apparatus of EP1562492 unusable for many procedures where clamping in confined cavities is required.

Other clamping or occlusion devices are known from the following: US2005/0113634, US2005/0113852, WO2009/048367, U.S. Pat. Nos. 6,582,451, 6,656,205, EP1878390, U.S. Pat. Nos. 4,800,879, 5,921,996, 4,120,302 and 5,697,942. However, at least some of the clamping or occlusion devices in these documents exhibit one or more of the aforementioned problems.

The reference to any prior art in this specification is not, and should not be taken as, an acknowledgement or any form of suggestion that the prior art forms part of the common general knowledge.

Object of the Invention

It is a preferred object of the invention to provide an improved surgical clamping device that addresses or at least ameliorates one or more of the aforementioned problems of the prior art and/or provides a useful commercial alternative.

SUMMARY OF THE INVENTION

Generally, the present invention relates to surgical clamping devices which reduce or minimize the likelihood of damage to the blood vessel being clamped compared with the prior art.

According to one aspect, but not necessarily the only aspect or the broadest aspect, the present invention resides in a clamping device for occluding a blood vessel, the device comprising:

a pair of jaws for receiving the blood vessel therebetween;
one or more inflatable membranes within the jaws; and
at least one handle coupled to the pair of jaws via a hollow arm;
wherein the at least one handle comprises an actuator coupled to the one or more inflatable membranes via the hollow arm for inflating the one or more inflatable membranes to occlude the blood vessel.

Suitably, each of the jaws comprises a curved profile.

Suitably, the jaws are detachable from the hollow arm.

Suitably, the jaws are fixed to the hollow arm.

Suitably, the jaws are adjustable relative to the hollow arm.

Suitably, the jaws are fixed relative to the hollow arm.

Suitably, the jaws can occupy one of a plurality of predetermined positions relative to the hollow arm.

Suitably, the jaws can occupy any position within a predetermined range of angles relative to the hollow arm.

Suitably, the clamping device can comprise a ratchet mechanism or gearing mechanism for securing the jaws at the predetermined angles.

Suitably, a length of the jaws is selectable from a plurality of predetermined lengths.

Suitably, the jaws and/or the hollow arm are rotatable and/or bendable.

Suitably, the actuator coupled to the inflatable membrane via the hollow arm controls deflation of the inflatable membrane to decrease the pressure exerted by the inflatable membrane.

Suitably, the inflatable membrane substantially forms a toroid or toroid-like shape when inflated.

Preferably, the membrane adjusts to the shape of the blood vessel to occlude the blood vessel.

Suitably, the jaws and/or the hollow arm and/or the handle are disposable (for single use) or are reusable.

Suitably, the hollow arm is flexible and can be adjusted to a range of different positions and orientations relative to the at least one handle.

Suitably, a length of the hollow arm is adjustable, e.g. telescopic.

Preferably, the clamping device comprises a non-return valve to keep the inflatable membrane inflated.

Suitably, the clamping device comprises a button, the actuation of which effects deflation of the inflatable membrane.

Some embodiments comprise a clamp head comprising a body and the pair of jaws extending from the body, wherein the clamp head is attachable to, and detachable from, an end of the hollow arm distal the handle.

Suitably, each jaw of the pair of jaws comprises an inner face having an inflatable membrane coupled thereto.

Suitably, the clamp head comprises at least one channel extending therethrough to each of the inflatable membranes.

Suitably, the clamp head comprises a shoulder extending rearward of the body; a projection extending rearward of the shoulder; a channel extending through the projection and part of the shoulder into a chamber comprising a biased check valve; and a channel extending between the chamber and each of the inflatable membranes.

The clamping device may further comprise a cable extending from the handle though the hollow arm and a claw coupled to an end of the cable distal the handle.

The clamping device may further comprise an actuator coupled to the cable, the actuator movable at least partially within the handle to extend the claw beyond an end face of the hollow arm for coupling with a recess between the shoulder and the projection of the clamp head to attach the clamp head to the hollow arm.

Suitably, the actuator in the handle comprises a movable trigger, which abuts a piston received within a channel in the handle, wherein the channel is in communication with the inflatable membranes via a pressure cavity and a first channel in the handle.

Suitably, the handle further comprises one or more of the following:
a pressure check valve housed within the pressure cavity;
an atmospheric check valve housed within a channel extending between the channel housing the piston and the atmosphere;
a pressure release valve between the pressure cavity and the atmosphere.

Further aspects and/or features of the present invention will become apparent from the following detailed description.

BRIEF DESCRIPTION OF THE DRAWINGS

In order that the invention may be readily understood and put into practical effect, reference will now be made to preferred embodiments of the present invention with reference to the accompanying drawings, wherein like reference numbers refer to identical elements. The drawings are provided by way of example only, wherein:

FIG. 4 is a plan view of the clamping device shown in FIG. 2 with the clamping head detached from the arm;

FIG. 5 is a sectional view of the clamping device shown in FIG. 4 along A-A;

FIG. 8 is a plan view of the clamping device shown in FIG. 2 with the clamping head attached to the arm;

FIG. 9 is a sectional view of the clamping device shown in FIG. 8 along A-A;

FIG. 10 is an enlarged perspective view of a portion of the arm and the clamping head with a blood vessel between jaws of the clamping head and an inflatable membrane deflated; and FIG. 11 shows the view of the clamping device in FIG. 10 with the inflatable membrane inflated such that the blood vessel is constricted.

Figure 1:
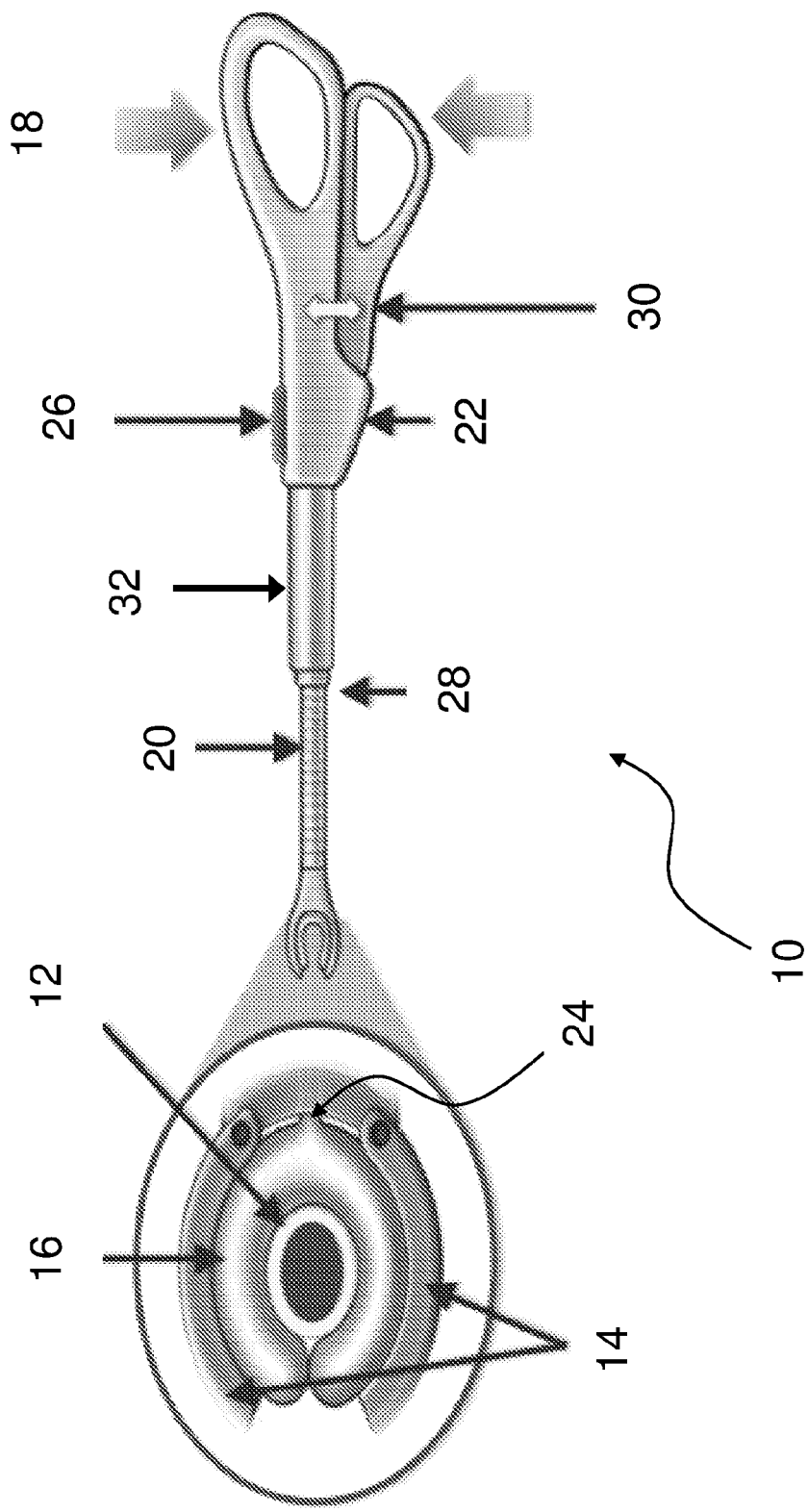
FIG. 1 is a side view of a clamping device according to a first embodiment of the present invention, which includes an enlarged view of a pair of jaws and an inflatable membrane of the clamping device.

Skilled addressees will appreciate that elements in the drawings are illustrated for simplicity and clarity and have not necessarily been drawn to scale. For example, the relative dimensions of some of the elements in the drawings may be distorted to help improve understanding of embodiments of the present invention.

DETAILED DESCRIPTION OF THE PREFERRED EMBODIMENTS

With reference to FIG. 1, a clamping device 10 for occluding a blood vessel 12 according to an embodiment of the present invention comprises a pair of jaws 14 for receiving the blood vessel 12 therebetween. An inflatable membrane 16 is provided within the jaws 14 and at least one handle 18 is coupled to the pair of jaws 14 via a hollow arm 20. The at least one handle 18 comprises an actuator 22 coupled to the inflatable membrane 16 via the hollow arm 20 for inflating the inflatable membrane to occlude the blood vessel 12.

In the embodiment shown in FIG. 1, each of the jaws 14 comprises a curved profile and one end of each of the jaws is pivotally coupled by any suitable means to an end of the hollow arm 20. Hence, the jaws 14 are adjustable relative to the hollow arm 20. For example, the jaws 14 can move further apart to accommodate larger blood vessels and move closer together to accommodate smaller blood vessels. In some embodiments, the jaws 14 can occupy any position within a predetermined range of angles relative to the hollow arm 20.

In some embodiments, the jaws 14 can occupy one of a plurality of predetermined positions relative to the hollow arm 20 to accommodate different sized blood vessels. The clamping device 10 may comprise a ratchet mechanism or gearing mechanism for securing the jaws 14 at the predetermined angles.

In some embodiments, an angle of orientation of the jaws 14 can be adjusted in one, two or three angular degrees of freedom and set by means of, for example, a friction hinge, a flexible material, or similar mechanism.

In some embodiments, the jaws 14 are detachable from the hollow arm 20, for example, for cleaning or repair or for disposal if the jaws 14 are a single use component. The jaws 14 can also be detachable to change between jaws 14 having different properties. In some embodiments the jaws 14 are detachable and remain in place occluding the blood vessel. The jaws 14 are re-attached to the hollow arm 20 for removal.

In some embodiments, a length and/or a degree of curvature and/or a shape of the jaws 14 is selectable from a plurality of predetermined lengths, degrees of curvature and shapes respectively.

The inflatable membrane 16 is affixed to an inside surface of the jaws 14 by any suitable means, such as gluing. When inflated, the membrane 16 adjusts to the shape of the blood vessel 12 to occlude the blood vessel 12. In particular, as the membrane 16 is inflated around the blood vessel 12, the membrane 16 adjusts to the shape required to occlude the blood vessel 12 without causing damage. For example, some blood vessels 12 have inflexible plaque lining their inner walls and the membrane 16 adjusts to the shape of the blood vessel 16 such that the risk of dislodging the plaque is minimised.

In some embodiments, the inflatable membrane 16 substantially forms a toroid or toroid-like shape when inflated which substantially surrounds a circumference of the blood vessel 12. In some embodiments, as shown in FIG. 1, the inflatable membrane 16 does not form a perfect toroid when inflated, such that there is a small gap between the outer surface of the blood vessel 16 and the surface of the inflatable membrane 16. However, the small gap does not impair the performance of the clamping device 10.

The inflatable membrane 16 can be made from any suitable material such as silicone, polymers or graphene. Other parts of the clamping device 10 can also be made from such materials or a combination thereof.

In some embodiments, a tube or conduit 24 is coupled to and communicates with the inflatable membrane 16. The tube/conduit 24 extends within the hollow tube 20 to the handle 18 where the tube/conduit 24 is coupled to the actuator 22. The actuator 22 coupled to the inflatable membrane 16 via the hollow arm 20 controls inflation of the inflatable membrane 16 to increase the pressure exerted by the inflatable membrane 16 on the blood vessel 12.

In some embodiments, the actuator 22 controls deflation of the inflatable membrane 16 to decrease the pressure exerted by the inflatable membrane 16 on the blood vessel 12. Alternatively, the clamping device 10 comprises a button 26, the actuation of which effects deflation of the inflatable membrane 16. In some embodiments, deflation of the inflatable membrane 16 can be controlled by the actuator 22 or the button 26 to provide improved safety.

In some embodiments, the clamping device 10 comprises a non-return valve 28 to keep the inflatable membrane 16 inflated. The non-return valve 28 ensures that fluid pumped into the inflatable membrane 16 cannot flow out thereby maintaining the membrane inflation pressure. However, the non-return valve 28 can be opened to release fluid from the membrane 16 thereby removing the clamping action on the blood vessel 12 by deflating the membrane 16. The non-return valve 28 can be opened by activating the button 26 on the handle 18. Examples of non-return valves include a flexible duckbill, a flap valve and a spring loaded ball check valve.

In some embodiments, a section including the inflatable membrane 16 can be detached from the clamping device 10. For example, the jaws 14 are detachable from the hollow arm 20 and/or the hollow arm 20 is detachable from the actuator 22. In these embodiments, the non-return valve 28 and/or another valve can be provided in the detachable section including the inflatable membrane 16 to ensure that fluid pumped into the inflatable membrane 16 cannot flow out when the section is detached.

In the embodiment shown in FIG. 1, squeezing the handles 18 activates the actuator 22 which inflates the membrane 16 with a fluid. The actuator 22 can comprise a pumping mechanism, examples of which include a piston and chamber system pumping the fluid, a bladder squeezed to inflate the membrane 16 with the fluid or a peristaltic system. As the membrane 16 inflates the membrane exerts pressure on the blood vessel 12. As inflation continues the membrane 16 closes on the blood vessel 12 until blood flow is occluded.

The handles 18 are squeezed by the user, for example, in a scissor action, to clamp the blood vessel 12 to the desired level of occlusion. When the handles 18 are released a spring mechanism 30 returns the handles 18 to the original position enabling the user to squeeze the handles 18 again and further inflate the membrane 16 if additional occlusive force is required.

In alternative embodiments, other manual inflation methods can be used. For example, pressing a convex rubber ball mounted on the handle 18 which forces the fluid into the membrane 16.

In embodiments of the invention, the fluid can be, for example, a liquid, a gel, air or an inert gas. Preferably, the fluid is non-toxic and sterile, for example, the fluid can be a saline solution or a saline gel.

In some embodiments, the hollow arm 20 is flexible and can be adjusted to a range of different positions and orientations relative to the at least one handle 18.

In some embodiments, a length of the hollow arm is adjustable, e.g. telescopic, such that the length of the hollow arm 20 can be selected and varied according to the particular procedure for which the clamping device 10 is being used.

In some embodiments, the hollow arm 20 comprises a rigid portion 32 coupled between the handle 18 and a flexible/extendible portion of the hollow arm 20. Rigid portion 32 can house sections of the hollow arm 20 which allow the arm 20 to telescope thus adjusting length.

In some embodiments, the jaws 14 and/or the hollow arm 20 are rotatable and/or bendable to assist in accessing difficult to access blood vessels 12.

In some embodiments, the jaws 14 and/or the hollow arm 20 and/or the handle 18 are disposable and therefore only intended for single use. Alternatively, one or more of the components of the clamping device 10 can be reusable.

In use, the user, e.g. a surgeon, inserts the blood vessel 12 between the two jaws 14 so that the inflatable membrane 16 can enclose the blood vessel. At this stage the inflatable membrane 16 is deflated or at least partially deflated. The user squeezes the handles 18 together until the blood flow in the vessel is reduced or ceases as required. If one squeeze of the handles 18 is insufficient the user can squeeze the handles 18 again until the blood vessel 12 is occluded to their satisfaction. If during the operation the occluded vessel 18 begins leaking the user can squeeze the handles again until the vessel is occluded. When finished the user slides the button 26 forward to deflate the membrane 16 and release the pressure on the blood vessel 12. The clamping device 10 can then be removed from the blood vessel 16.

A clamping device 110 for occluding blood vessels according to another embodiment of the present invention will now be described with reference to FIGS. 2 to 11.

Figure 3:
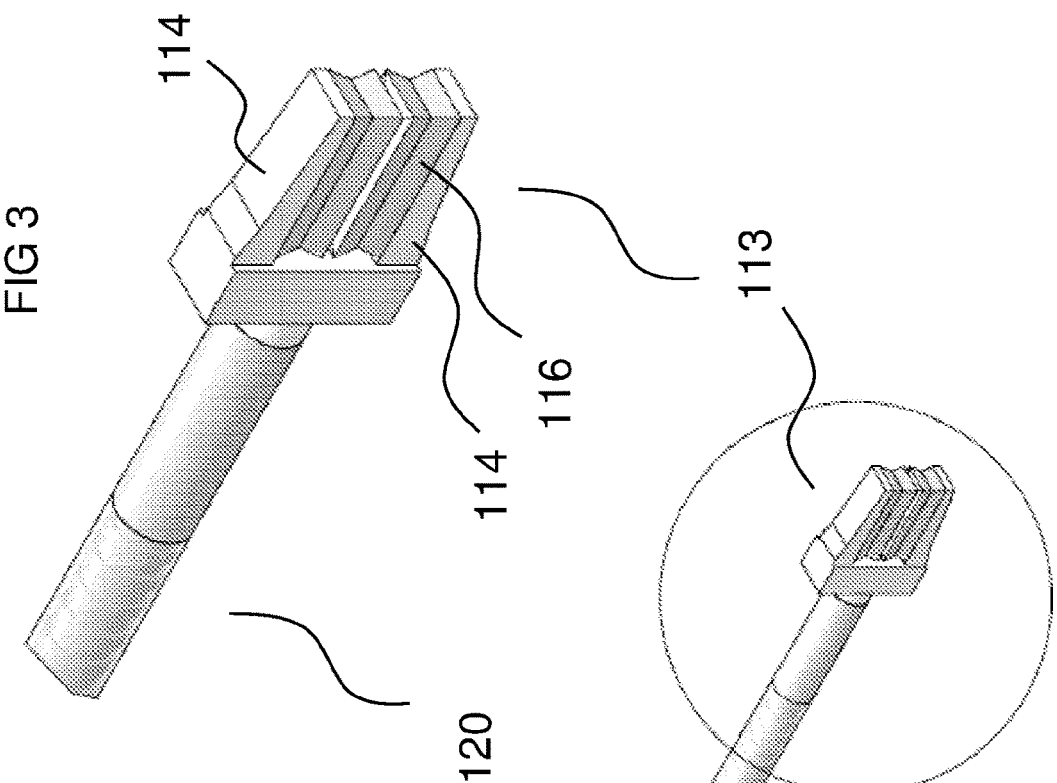
FIG. 3 is an enlarged perspective view of a clamping head and a portion of an arm of the clamping device shown in FIG. 2.
Figure 2:
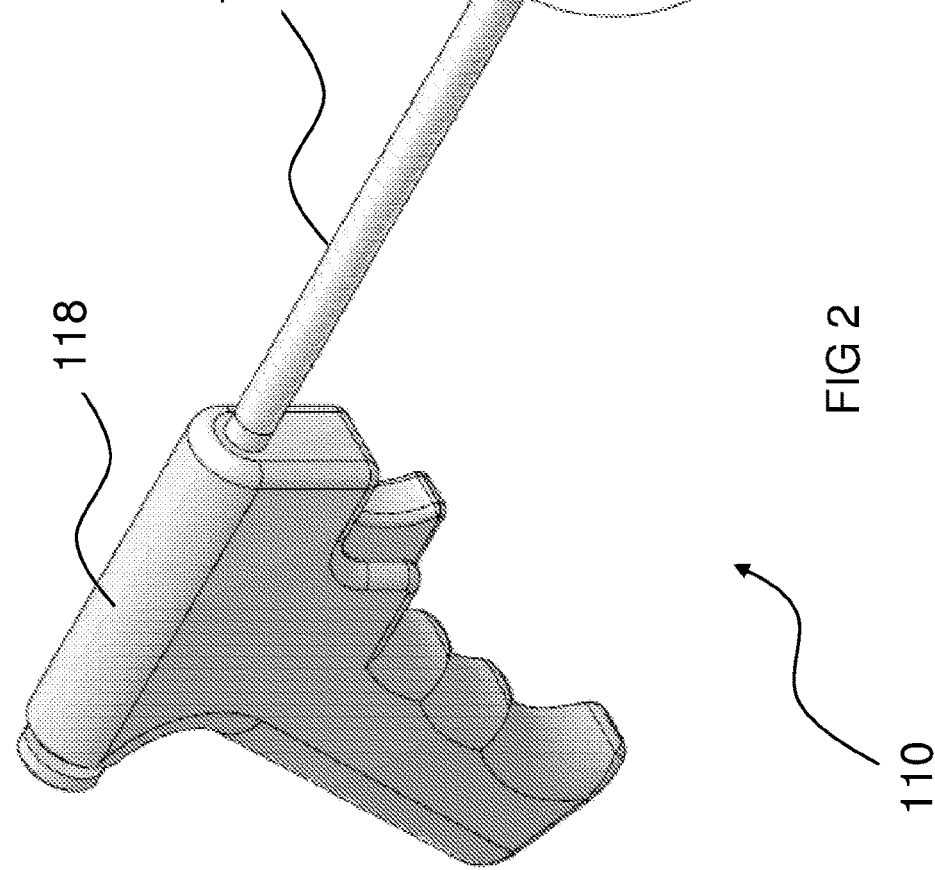
FIG. 2 is perspective view of a clamping device according to a second embodiment of the present invention.

With reference to FIGS. 2 and 3, the clamping device 110 comprises a handle 118, an arm 120 coupled to the handle 118 and a clamp head 113, which is attachable to and detachable from an end of the arm 120 distal from the handle 118. The handle 118 is held by the operator while using the clamping device 110. While holding the device, the operator can attach and detach the clamp head 113. While holding the device, the operator can pressurise and depressurise one or more inflatable membranes 116 of the clamp head 113 to occlude the blood vessel and to stop occlusion of the blood vessel respectively. In the embodiment shown, each jaw 114 of the pair of jaws of the clamp head 113 comprises an inner face having an inflatable membrane 116 coupled thereto by any suitable means in the art.

The mechanisms for attaching and detaching the clamp head 113 and pressurising and depressurising the one or more inflatable membranes 116 are described in further detail herein.

The arm 120 acts as an extension to the clamping device 110 which allows access to difficult to reach and crowded areas/regions of the body through relatively small incisions. In preferred embodiments, the arm 120 is bendable with a memory to assist further in reaching areas and regions of the body that are difficult to access.

FIGS. 4 and 5 show a plan view and a cross sectional view respectively of the clamping device 110 with the clamp head 113 detached from the arm 120. The handle 118 comprises a first channel 138 which receives an actuator in the form of a button 140 and a biasing element 142, such as a helical spring. A shaft 146 of the button 140 comprises a circumferential recess 148 for receiving a sealing element 150, such as an elastomeric seal and a circlip, to provide an airtight seal between the button 140 and the channel 138.

The handle 118 comprises a second channel 152 which receives arm 120, which in this embodiment is hollow. The handle 118 comprises a third channel 154 which extends between the first channel 138 and the second channel 152. Third channel 154 is of a narrower diameter than the diameters of the first channel 138 and the second channel 152. Third channel 154 allows the passage therethrough of an actuator in the form of a cable 156, such as a Bowden cable, from the first channel 138 into the hollow arm 120, which is received within the second channel 152. When in the form of Bowden cable, cable 156 comprises inner cable 156 and an outer in the form of spiral tube 220. Cable 156 is coupled to the button 140 and extends through the hollow arm 120 and is coupled at an end of the arm 120 distal from the handle 118 to a claw 160 for attachment to the clamp head 113.

Figure 6:
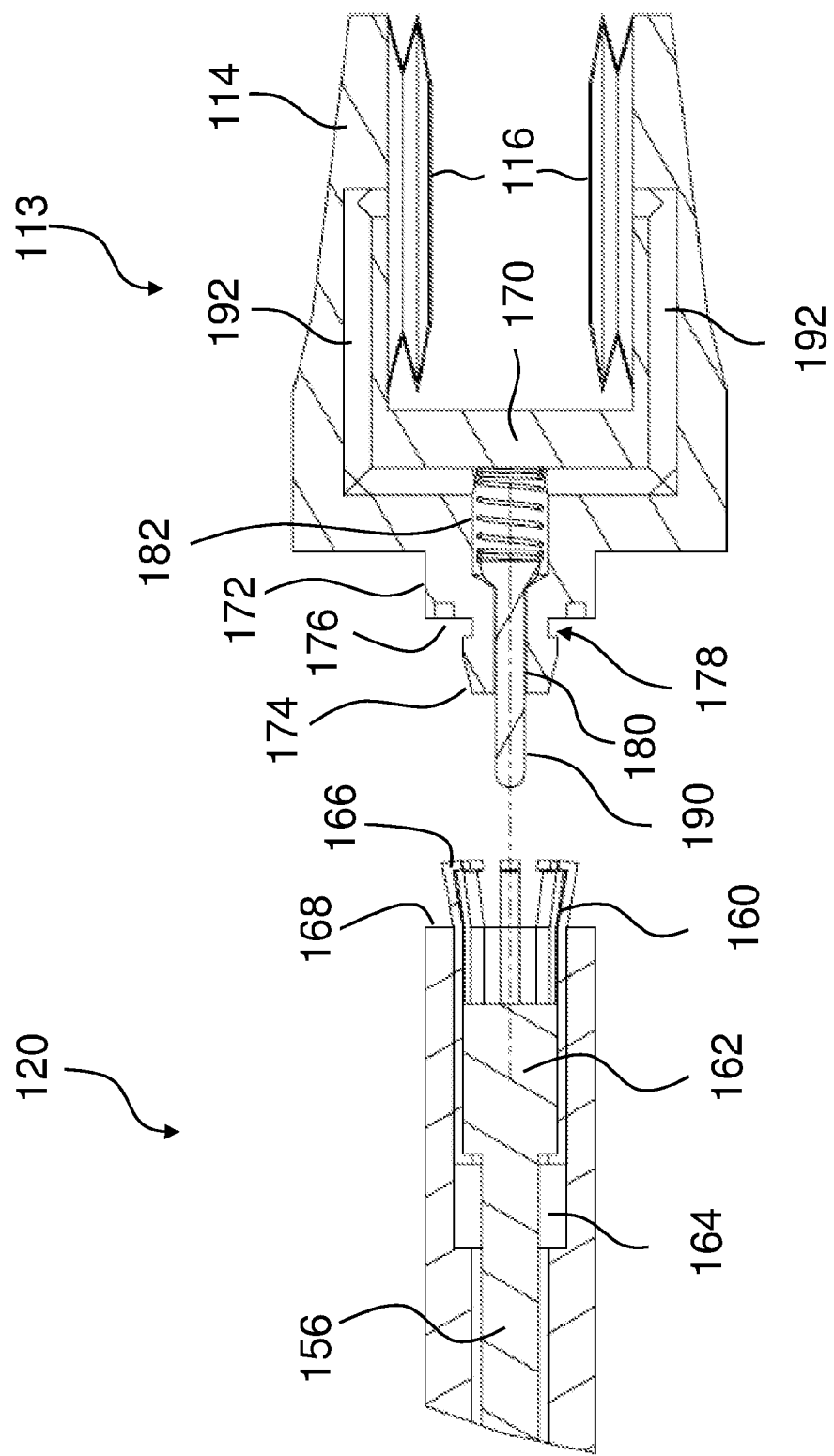
FIG. 6 is an enlarged sectional view of the clamping head detached from the arm.

The clamp head 113, the arm 120 and the attachment of the head 113 to the arm 120 will now be described in further detail with reference to the enlarged cross sectional views shown in FIGS. 6 and 7.

A bearer block 162 is coupled to an end of the cable 156 and the claw 160 is coupled to the end of the cable 156 via the bearer block 162. The bearer block 162 and the claw 160 are accommodated within a cavity 164 at the end of the arm 120. Claw 160 comprises a plurality of fingers 166 which are biased outwards from a central axis of the arm 120. Arm 120 comprises an end face 168.

Clamp head 113 comprises a body 170 and a pair of jaws 114 extending from the body 170. In some embodiments the pair of jaws 114 is rigid and in a fixed relationship with the body 170. In other embodiments, the pair of jaws 114 is movable relative to the body 170 of the clamp head 113, as represented by the dotted lines shown in FIG. 7. For example, in some embodiments the jaws 114 can pivot relative to the body 170 about an axis aligned with the vertical portions of the channels 192.

A shoulder 172 extends rearward of the body 170 and a projection 174 extends rearward of the shoulder 172. Clamp head 113 comprises a circumferential seal 176 in the shoulder 172 and a circumferential recess 178 between the shoulder 172 and the projection 174. Clamp head 113 comprises a channel 180 extending through the projection 174 and part of the shoulder 172. Channel 180 opens into a chamber 182 in the body 170 of the clamp head 113 for accommodating a check valve 184 and a biasing element 186, such as a helical spring. Clamp head 113 comprises a valve seat 188 at the interface between the channel 180 and the chamber 182 for receiving the check valve 184. Check valve 184 comprises a pin 190 which extends through and protrudes from the channel 180. Body 170 and jaws 114 comprise channels 192 which extend between the chamber 182 and the inflatable membranes 116 coupled to the jaws 114. Channels 192 communicate air to and from the inflatable membranes 116 to inflate and deflate the inflatable membranes 116 as described herein.

To attach the clamp head 113 to the arm 120, the operator depresses the button 140 in the handle 118, i.e. towards the clamp head 113. This motion compresses biasing element 142 and pushes the inner of the cable 156, and thus the bearer block 162 and the claw 160, towards the distal end of the arm 120. This motion causes part of the claw 160 and the fingers 166 of the claw to protrude from the end face 168 of the arm 120. In the absence of the constraint of the cavity 164, the fingers 166 of the claw 160 open as they are sprung outwards from the centre axis of the arm 120. The splayed fingers 166 protruding from the end face 168 of the arm 120 are shown in FIGS. 4 to 6.

The fingers 166 of the claw 160 are positioned adjacent to the recess 178 in the clamp head 113 and the button 140 is released. Button 140 is pushed back to its rest position by biasing element 142. This action moves the inner of the cable 156 attached to the button 140 towards the handle 118. The rearward movement of the cable 156 pulls the claw 160 back into the cavity 164 thus constraining the fingers 166 of claw 160 axially around the recess 178. The clamp head 113 attached to the arm 120 is shown in FIG. 7.

The motion of the cable 156 toward the handle 118 and engagement of the claw 160 with the recess 178 also forces the valve pin 190 against the bearer block 162. This moves the valve pin 190 away from the valve seat 188 and allows air flow from the arm 120 into the channels 192 of the clamp head 113. The motion of the cable 156 toward the handle 118 and engagement of the claw 160 with the recess 178 also compresses the seal 176 towards the end face 168 of the arm 120 and creates a seal between the arm 120 and the clamp head 113.

Inflation and deflation of the inflatable membranes 116 will now be described with reference to FIGS. 8 to 11.

The handle 118 of the clamping device 110 comprises an actuator in the form of a movable trigger 200, which abuts piston 202 received with a channel 204 in the handle 118. A biasing element 206, such as a helical spring, is also received within the channel 204 and biases the piston 202 out of the channel 204. A pressure cavity is formed by channel 208 extending between channel 204 and the first channel 138. The pressure cavity includes a pressure check valve 210. An atmospheric check valve 212 is housed within a channel 214 extending between the channel 204 (housing the piston 202) and the atmosphere. The handle 118 also comprises a pressure release valve 218 between the channel 208 and the atmosphere.

The operator positions the blood vessel 112 between the jaws 114 of the clamp head 113 with inflatable membranes in a deflated state. The operator depresses trigger 200 which in turn depresses piston 202 against biasing element 206.

The increase in pressure in the channel 204 opens the pressure check valve 210 in the channel 208 and air flows through the channel 208 and into the first channel 138. The air flows through the arm 120 in the gap between the cable 156 and an outer wall of the arm 120. The air flows through the channel 180 and the open check valve 184, through channels 192 in the jaws 114 and into the inflatable membranes 116. The increase in pressure inflates the membranes and the membranes apply an occluding force to the blood vessel 112. When the trigger 200 is released, biasing element 206 pushes piston 202 against the back of trigger 200. This retraction of the piston 202 creates a vacuum which closes pressure check valve 210 and opens atmospheric check valve 212. The increased pressure is maintained in the pressure cavity formed by channel 208 and atmospheric pressure is behind the piston 202.

The occluding force applied by the inflated membranes 116 can be increased by the operator following this same procedure one or more times until the desired occlusion force is reached.

The occlusion force can be decreased by the operator pressing pressure release valve 218. This allows air in the pressure cavity formed by channel 208 to escape to atmosphere thus allowing the inflated membranes 116 to retract thus reducing the occlusion force.

The pressure in the pressure cavity formed by channel 208 should be released to atmosphere before detaching the clamp head 113 from the arm 120.

In some embodiments, the inflatable membranes 116 have a concertina-type or bellows-type construction comprising one or more folds as shown which assist in inflation and deflation of the inflatable membranes 116.

Figure 7:
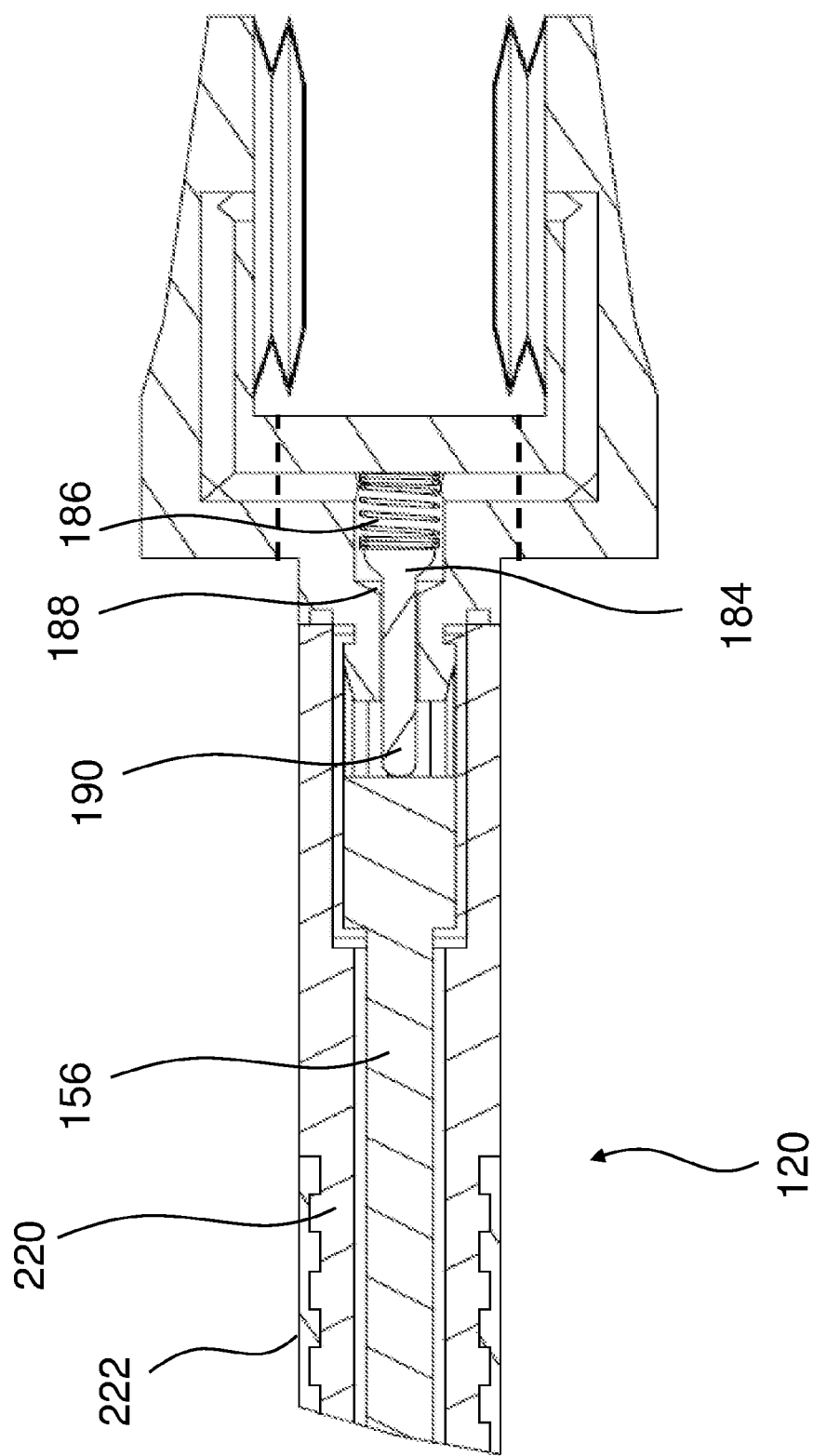
FIG. 7 is an enlarged sectional view of the clamping head attached to the arm.

With reference to FIG. 7, the arm 120 comprises a spiral tube 220 and flexible skin 222, which enables the arm 120 to be manipulated manually into different positions. Once manipulated into the desired position the arm 120 will stay in this position unit manipulated again. This allows the shape of the arm 120 to be tailored to the region to be accessed.

The smooth flexible skin 222 of the arm 120 enables the arm 120 to be easily cleaned.

Hence, embodiments of the present invention provide solutions for alleviating at least some of the problems of the prior art. The one or more inflatable membranes 16, 116 prevent excessive pressure and force being applied to the blood vessel 12, 112 whilst ensuring that occlusion has occurred before commencing with the next stage of the surgical procedure. The one or more inflatable membranes 16, 116 adjust to individual blood vessel morphology and the inflation of the one or more membranes 16, 116 can be accurately controlled to achieve the desired level of pressure. This can lower the clamping force required to occlude the blood vessel 12, 112, mitigate the dislodgement of plaque from the walls of the blood vessel 12, 112 and reduce the risk of damage to the blood vessel 12, 112.

Because the one or more inflatable membranes 16, 116 naturally adjust to the shape and size of the blood vessel 16, 116, a single clamping head 113 having jaws 114 of a fixed separation covers a range of blood vessels expected to be clamped in vascular surgical procedures. In other embodiments, only a small number of different size jaws 14, 114 is required to cover the range of blood vessels expected to be clamped in vascular surgical procedures. For example, it is envisioned that all blood vessel sizes in the range of 0.02 mm to 2.0 cm could be clamped using only 3 different sizes of jaws.

With the one or more inflatable membranes 16, 116 the force being applied to the blood vessel 12, 112 is limited to the pressure that can be applied to the one or more inflatable membranes 16, 116, thus avoiding the possibility of highly leveraged and uncontrolled forces being applied to the blood vessel out of control.

Because the one or more inflatable membranes 16, 116 is inflated using an actuator, such as a pump without discrete increments, or the trigger 200 and channel arrangement, an almost continuous increase and decrease in force can be applied to the blood vessel 12, 112. This avoids the small number of discrete increments available to the surgeon using traditional clamps, and provides a very fine level of adjustment. Embodiments of the present invention can also have a low mechanical advantage between the actuator 22, 200 and the one or more inflatable membranes 16, 116 providing finer pressure feedback at the handle 18, 118 or trigger 200. The one or more inflatable membranes 16, 116 also provide a softer surface against the blood vessel 12, 112 than the metallic surface of many prior art clamps.

Embodiments comprising detachable jaws provide an improved surgical clamping kit which is adaptable to a wide range of surgical procedures and the clamping of a variety of blood vessels. The detachable jaws 14, or detachable clamping head 113 comprising jaws 114 can be single use or reusable and can be selected as required for the particular procedure.

The flexible hollow arm 20 having an adjustable length and flexible hollow arm 120 enable the clamping device 10, 110 to be used and controlled at a distance, for example, in regions that are difficult to reach, such as deeper body cavities, or are obstructed. Greater flexibility of the shape and/or length of the hollow arm 20, 120 is possible than with a fulcrum type clamp as the pressure on the blood vessel 12 is controlled via a fluid which is pumped through the hollow arm 20 rather than by a solid mechanical connection.

In this specification, the terms "comprise", "comprises", "comprising" or similar terms are intended to mean a non-exclusive inclusion, such that a system, method or apparatus that comprises a list of elements does not include those elements solely, but may well include other elements not listed.

Throughout the specification the aim has been to describe the preferred embodiments of the invention without limiting the invention to any one embodiment or specific collection of features. It is to be appreciated by those of skill in the art that various modifications and changes can be made in the particular embodiments exemplified without departing from the scope of the present invention. For example, those of skill in the art will appreciate that features of separate embodiments described herein may be combined where applicable and are intended to fall within the scope of the present invention.

The invention claimed is:

1. A clamping device for occluding a blood vessel, the device comprising:
   a pair of jaws for receiving the blood vessel therebetween;
   one or more inflatable membranes within the jaws;
   at least one handle coupled to the pair of jaws via a hollow arm; and
   a clamp head comprising a body and the pair of jaws extending from the body, wherein the clamp head is attachable to, and detachable from, an end of the hollow arm distal the handle
   wherein the at least one handle comprises an actuator coupled to the one or more inflatable membranes via the hollow arm for inflating the one or more inflatable membranes to occlude the blood vessel.

2. The clamping device of claim 1, wherein each of the jaws comprises a curved profile.

3. The clamping device of claim 1, wherein the jaws possess one or more of the following characteristics:
   are detachable from the hollow arm;
   are adjustable relative to the hollow arm;
   can occupy one of a plurality of predetermined positions relative to the hollow arm;
   can occupy any position within a predetermined range of angles relative to the hollow arm;
   have a length selectable from a plurality of predetermined lengths.

4. The clamping device of claim 1, wherein the jaws and/or the hollow arm are rotatable and/or bendable.

5. The clamping device of claim 1, wherein the one or more inflatable membranes substantially forms a toroid or toroid-like shape when inflated.

6. The clamping device of claim 1, wherein the one or more inflatable membranes adjust to the shape of the blood vessel to occlude the blood vessel.

7. The clamping device of claim 1, wherein a length of the hollow arm is adjustable, e.g. telescopic, and/or the hollow arm is flexible and can be adjusted to a range of different positions and orientations relative to the at least one handle.

8. The clamping device of claim 1, further comprising a non-return valve to keep the inflatable membrane inflated.

9. The clamping device of claim 1, further comprising a button, the actuation of which effects deflation of the inflatable membrane.

10. The clamping device of claim 1, wherein each jaw of the pair of jaws comprises an inner face having one of the inflatable membranes coupled thereto.

11. The clamping device of claim 1, wherein the clamp head comprises at least one channel extending therethrough to each of the inflatable membranes.

12. The clamping device of claim 11, wherein the clamp head comprises:
   a shoulder extending rearward of the body;
   a projection extending rearward of the shoulder;
   a channel extending through the projection and part of the shoulder into a chamber comprising a check valve; and
   a channel extending between the chamber and each of the inflatable membranes.

13. The clamping device of claim 1, further comprising a cable extending from the handle though the hollow arm and a claw coupled to an end of the cable distal the handle.

14. The clamping device of claim 13, further comprising an actuator coupled to the cable, the actuator movable at least partially within the handle to extend the claw beyond an end face of the hollow arm for coupling with a recess between the shoulder and the projection of the clamp head.

15. The clamping device of claim 14, wherein the handle further comprises one or more of the following:
   a pressure check valve housed within the pressure cavity;
   an atmospheric check valve housed within a channel extending between the channel housing the piston and the atmosphere;
   a pressure release valve between the pressure cavity and the atmosphere.

16. The clamping device of claim 1, wherein the actuator in the handle comprises a movable trigger, which abuts a piston received within a channel in the handle, wherein the channel is in communication with the inflatable membranes via a pressure cavity and a first channel in the handle.

* * * * *